(12) United States Patent
Stierli et al.

(10) Patent No.: US 9,051,272 B2
(45) Date of Patent: Jun. 9, 2015

(54) PROCESS FOR THE PREPARATION OF PHENYL SUBSTITUTED 3-DIFLUOROMETHYL-1-METHYL-1H-PYRAZOLE-4-CARBOXYLIC ACID N-METHOXY-[1-METHYL-2 PHENYLETHYL] AMIDES

(71) Applicant: Syngenta Participations AG, Basel (CH)

(72) Inventors: Daniel Stierli, Stein (CH); Harald Walter, Stein (CH); Michael Rommel, Monthey SA (CH); Reinhard Georg Hanreich, Munchwilen (CH); Martin Zeller, Münchwilen (CH); Thomas Vettiger, Münchwilen (CH); Tomas Smejkal, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/374,547
(22) PCT Filed: Feb. 26, 2013
(86) PCT No.: PCT/EP2013/053773

§ 371 (c)(1),
(2) Date: Jul. 25, 2014

(87) PCT Pub. No.: WO2013/127764

PCT Pub. Date: Sep. 6, 2013

(65) Prior Publication Data

US 2015/0018562 A1    Jan. 15, 2015

(30) Foreign Application Priority Data

Feb. 28, 2012    (EP) .................................... 12157354

(51) Int. Cl.
*C07D 231/12*    (2006.01)
*C07D 231/14*    (2006.01)

(52) U.S. Cl.
CPC ............ *C07D 231/12* (2013.01); *C07D 231/14* (2013.01)

(58) Field of Classification Search
CPC ..................................................... C07D 231/12
USPC ...................................................... 548/374.1
See application file for complete search history.

(56) References Cited

FOREIGN PATENT DOCUMENTS

| EP | 0810195 | 12/1997 |
| WO | 0034229 | 6/2000 |
| WO | 2010063700 | 6/2010 |

OTHER PUBLICATIONS

Li Lia et al, "Facile synthesis of 1-Aryl-s-propanones from Aromatic Amine," Synthetic Communications: An International Journal for Rapid Communication of Synthetic Organic Chemistry, Taylor & Francis Inc., Philadelphia, PA, Dec. 31, 2007, 37(6): 985-991.
International Search Report dated Mar. 26, 2013 for International Patent Application No. PCT/EP2013/053773.

*Primary Examiner* — Samantha Shterengarts
(74) *Attorney, Agent, or Firm* — R. Kody Jones

(57) ABSTRACT

The invention relates to a process for the preparation of a compound of formula (I), wherein $R_1$, $R_2$ and $R_3$ are as defined in claim 1, which process comprises a) adding a compound of formula (II), in the presence of an inert organic solvent to a mixture comprising an organic nitrite of formula (III) ($R_4$—O—N=O (III)), wherein $R_4$ is $C_1$-$C_8$alkyl, a compound of formula (IV), and an inert organic solvent; b) reacting the resulting compound of formula (V), with $H_2N$—O—$CH_3$ to the compound of formula (VII), c) reducing the compound of formula (VII) to the compound of formula (VIII), d) and reacting the compound of formula VIII with a compound of formula (IX), in which R* is halogen, hydroxy or $C_{1-6}$ alkoxy, to the compound of formula (I).

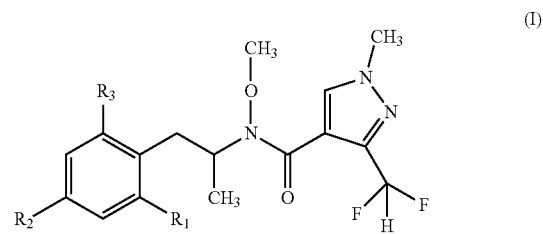

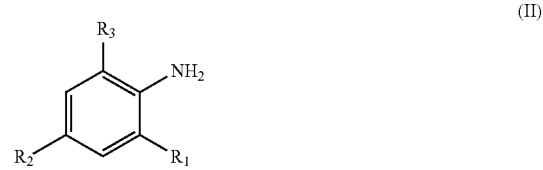

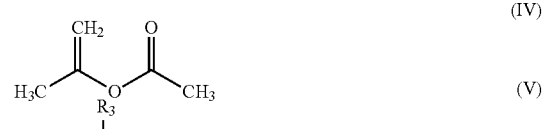

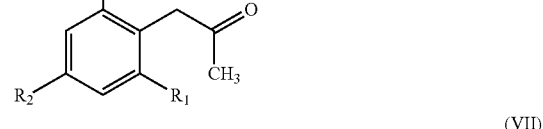

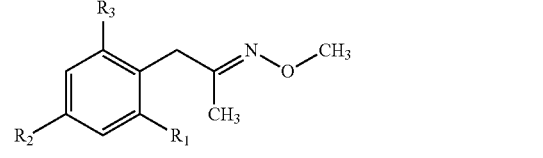

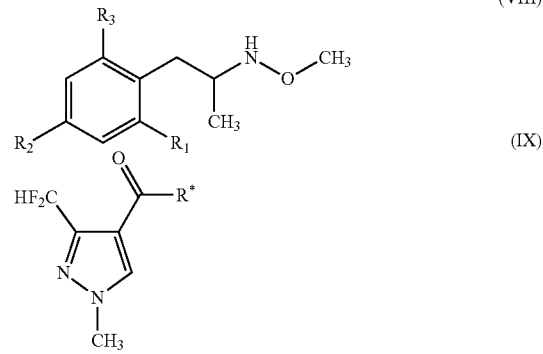

5 Claims, No Drawings

PROCESS FOR THE PREPARATION OF PHENYL SUBSTITUTED 3-DIFLUOROMETHYL-1-METHYL-1H-PYRAZOLE-4-CARBOXYLIC ACID N-METHOXY-[1-METHYL-2 PHENYLETHYL] AMIDES

RELATED APPLICATION INFORMATION

This application is a 371 of International Application No. PCT/EP2013/053773, filed Feb. 26, 2013, which claims priority to EP Patent Application No. 12157354.7, filed Feb. 28, 2012, the contents of which are incorporated herein by reference herein.

The present invention relates to a process for the preparation of carboxamides, in particular to the preparation of phenyl-substituted 3-difluoromethyl-1-methyl-1H-pyrazole-4-carboxylic acid methoxy-[1-methyl-2-phenyl-ethyl]-amides.

Phenyl-substituted 3-difluoromethyl-1-methyl-1H-pyrazole-4-carboxylic acid methoxy-[1-methyl-2-phenyl-ethyl]-amides and their microbiocidal properties are described for example in WO 2010/063700.

It is known from WO 2010/063700 to prepare phenyl-substituted 3-difluoromethyl-1-methyl-1H-pyrazole-4-carboxylic acid methoxy-[1-methyl-2-phenyl-ethyl]-amides (Ia) according to reaction scheme 1 starting from commercially available 2,4,6-trisubstituted benzoic acid of formula IVa. This starting material is very expensive, in particular if R signifies chloro, and the known process is therefore less suitable for large-scale production of 3-difluoromethyl-1-methyl-1H-pyrazole-4-carboxylic acid methoxy-[1-methyl-2-phenyl-ethyl]-amides. A further disadvantage of this prior art process is the significant number of reaction steps which makes this process uneconomical.

The synthesis of the compound of formula IIa, which can be reacted with the corresponding pyrazole derivative to 3-difluoromethyl-1-methyl-1H-pyrazole-4-carboxylic acid methoxy-[1-methyl-2-phenyl-ethyl]-amide derivatives (Ia), is described in scheme 1.

The disclosed reaction steps are as follows:
a) (Va), (VIa), (VIIa), (VIIIa) and (IXa);
b) (Va), (VIa), (VIIa), (VIIIa), (Xa) and (IXa);
c) (Va), (XIa), (XIIa), (Xa) and (IXa) or
d) (Va), (XIa), (XIIa), (VIIIa) and (IXa).

Reaction scheme 1: prior art process (R is an organic substituent):

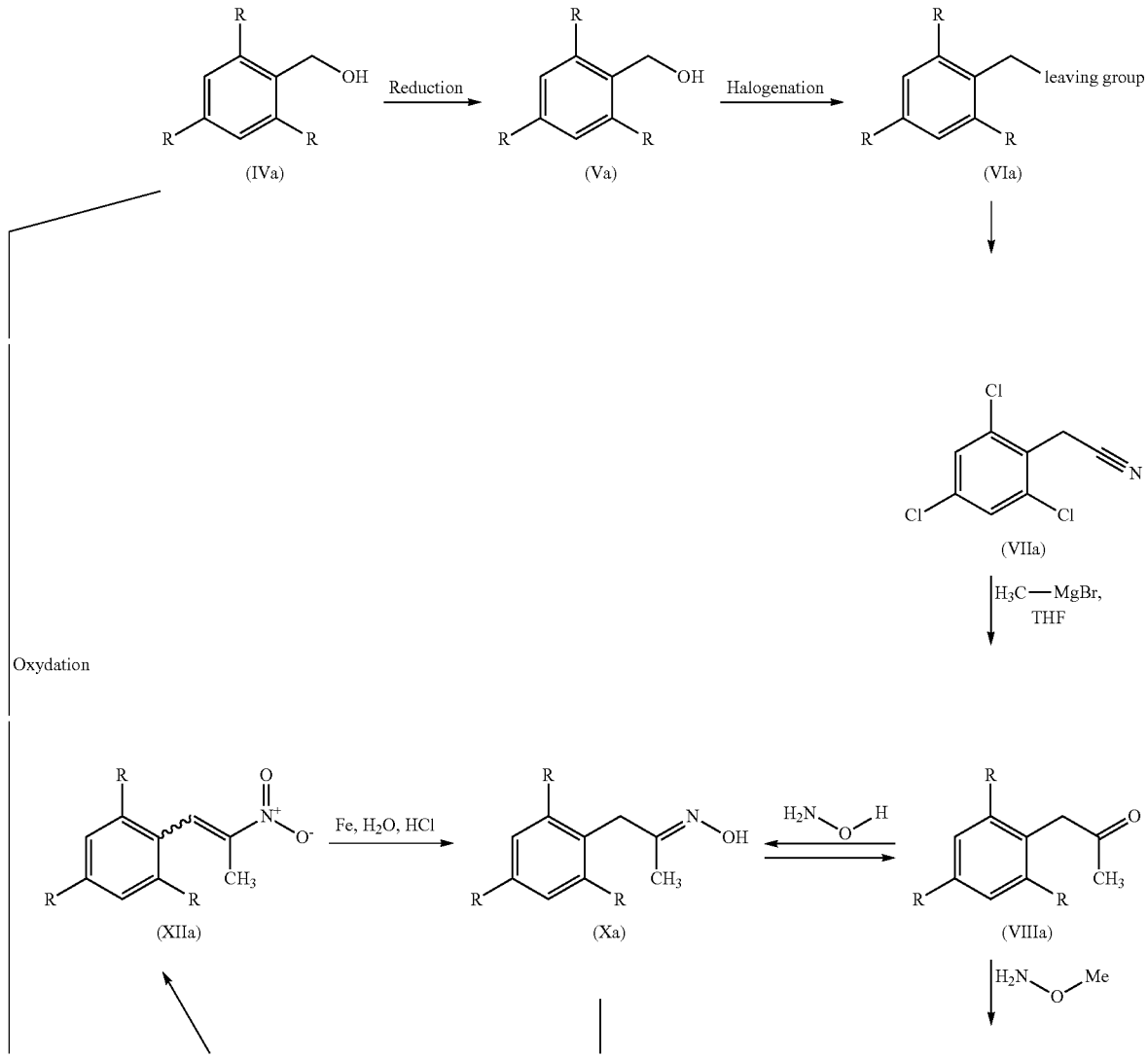

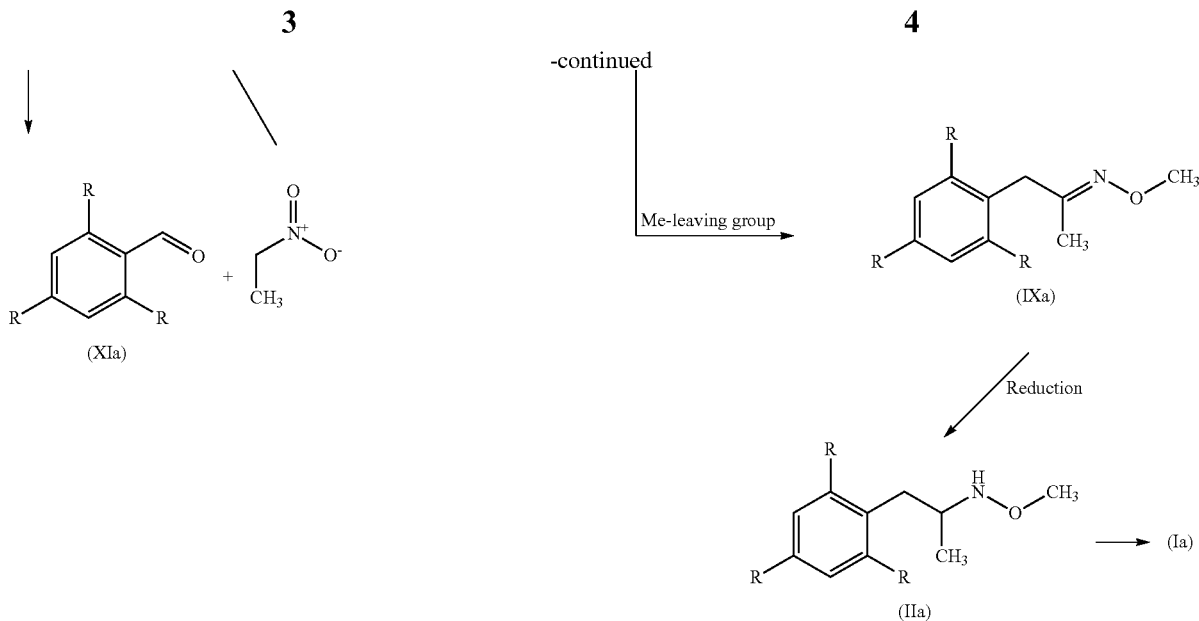

The aim of the present invention is therefore to provide a novel process for the production of
phenyl-substituted 3-difluoromethyl-1-methyl-1H-pyrazole-4-carboxylic acid methoxy-[1-methyl-2-phenyl-ethyl]-amides that avoids the disadvantages of the known process and makes it possible to prepare said compounds in high yields and good quality in an economically advantageous way with less reaction steps.

Thus, according to the present invention, there is provided a process for the preparation of the compound of formula I

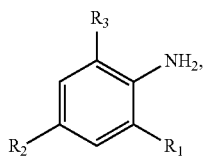
(I)

wherein
$R_1$ is hydrogen, halogen or $C_1$-$C_6$alkyl;
$R_2$ is hydrogen, halogen, $C_1$-$C_6$alkyl, $C_2$-$C_6$alkenyl, $C_3$-$C_6$alkinyl, $C_3$-$C_6$cycloalkyl-$C_3$-$C_6$alkinyl, halophenoxy, halophenyl-$C_3$-$C_6$alkinyl, $C(C_1$-$C_4$alkyl$)$=NO—$C_1$-$C_4$alkyl, $C_1$-$C_6$haloalkyl, $C_1$-$C_6$haloalkoxy, $C_2$-$C_6$haloalkenyl or $C_2$-$C_6$haloalkenyloxy; and
$R_3$ is hydrogen, halogen or $C_1$-$C_6$alkyl;
which process comprises
a) adding a compound of formula II

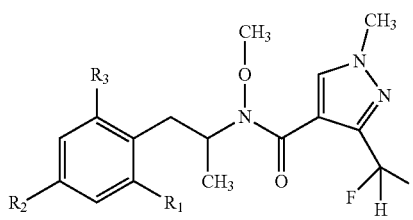
(II)

wherein $R_1$, $R_2$ and $R_3$ have the meanings as described under formula I, in the presence of an inert organic solvent to a mixture comprising an organic nitrite of formula III $$R_4\text{—O—N}=\text{O} \qquad (III),$$

wherein $R_4$ is $C_1$-$C_8$alkyl, a compound of formula IV

(IV)

and an inert organic solvent;
b) reacting the resulting compound of formula V

(V)

wherein $R_1$, $R_2$ and $R_3$ have the meanings as described under formula I with O-methyl-hydroxylamine of formula VI $$H_2N\text{—O—CH}_3 \qquad (VI),$$

to the compound of formula VII

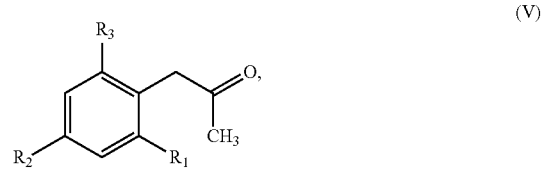
(VII)

wherein $R_1$, $R_2$ and $R_3$ have the meanings as described under formula I;

c) reducing the compound of formula VII to the compound of formula VIII

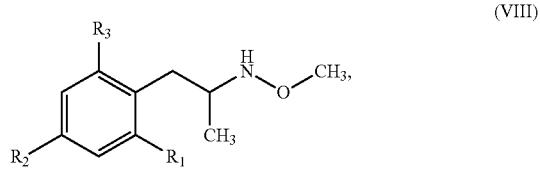

(VIII)

wherein $R_1$, $R_2$ and $R_3$ have the meanings as described under formula I d) and reacting the compound of formula VIII with a compound of formula IX

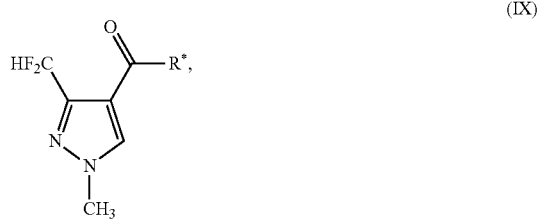

(IX)

in which R* is halogen, hydroxy or $C_{1-6}$ alkoxy, to the compound of formula I.

a) WO 00/34229 describes a process for the preparation of a ketone of formula V by diazotizing an aniline of formula II and reacting the resulting diazonium salt with isopropenylacetate of formula IV. A disadvantage of this process is the accumulation of the very reactive diazonium salt in the reaction mixture. Diazonium salts in general are sensitive to physical agents such as heat, light, shock, static electricity and dehydration that can lead to rapid, uncontrollable decompositions and explosions.

A further disadvantage is that 2 different equipments are needed to perform the reactions.

The process according to the invention uses easily accessible starting material, without the need of isolation or accumulation of diazonium salt and is therefore especially suitable for the large-scale preparation of a compound of formula I.

The compound of formula V can be prepared preferably by a one pot reaction adding the aniline of formula II to a mixture of isoprenylacetate of formula IV, an organic nitrite of formula III and a solvent. In preferred compounds of formula III, $R_4$ is $C_4$-$C_7$alkyl. A preferred nitrite is tert-butyl nitrite and tert.-amyl nitrite.

The mixture of isoprenylacetate of formula IV, an organic nitrite of formula III and a solvent can additionally contain a copper compound which can be advantageous to increase yield and/or quality of the product. Preferred copper compounds are CuO, $CuCl_2$ or $CuSO_4$. The amount of the copper compounds is preferably is 1-20 mol % in the relation to the aniline of formula II. Advantageous for the reaction is a temperature of −10° C. to 50° C. No isolation or accumulation of diazonium salt is required for this process step. Advantageously the same solvent is used for the aniline of formula II and the mixture of isoprenylacetate of formula IV and the organic nitrite of formula III. Suitable inert organic solvents are for example ketones, for example acetone, methylethylketone (MEK) or nitriles, for example acetonitrile. Preferred solvents are acetone and acetonitrile. The reaction without the use of copper can be environmentally more advantageous since copper waste can be avoided. Therefore, this process variant represents one of the preferred embodiments of this invention.

The compounds of formula II and III are either known or can be prepared according to methods well known in the art. Some compounds of formula II are commercially available, e.g. the compound of formula II, wherein $R_1$, $R_2$ and $R_3$ is chloro. Isoprenylacetate of formula IV is also commercially available.

b) The compound of formula VII can be prepared preferably by a one pot reaction adding a salt of O-methyl-hydroxylamine; preferably the hydrochloride salt as aqueous solution to the compound of formula V in an inert solvent such as methanol or ethanol. Advantageous for this reaction is a temperature of 10-90° C.; preferably 40-60° C. The compound of formula VII can be furthermore purified by extraction into a suitable solvent such as hexane, methylcyclohexane or toluene.

c) The compound of formula VIII can be obtained by reduction from the compound of formula VII by treatment with a borane reagent such as sodium cyano borohydride, complexes of borane e.g. complexes of borane with organic amines, such as complexes of borane with triethylamine, trimethylamine, pyridine or 5-ethyl-2-methylpyridine in a suitable solvent such as an organic acid like acetic acid, or such as an organic alcohol like methanol, ethanol or isopropanol and optionally in the presence of a strong acid, such as hydrogen chloride or sulphuric acid.

The compound of formula VIII can be also prepared by hydrogenation of a compound of formula VII in the presence of a catalyst containing a transition metal such at Pt in a suitable solvent and in the presence of at least 1 mol equivalent of a strong acid such as hydrogen chloride or sulphuric acid in a solvent such as an organic alcohol like methanol or acetic acid. Suitable temperatures include −10 to 60° C., preferably −10 to 30° C., and a hydrogen pressure of 0-0.1 MPa; preferably 0.3-0.5 MPa in particular 0.1-3 MPa, preferably 0.2-1 MPa.

d) The compound of formula I is prepared by reacting a compound of formula VII with a compound of formula (IX) with an excess of the compound of formula IX, advantageously in a ratio of 1:1 to 1:1.2. R* is preferably chloro. The reaction is advantageously performed in an inert solvent in the presence of a base. Such suitable solvents are for example dichloromethane, xylene, toluene or ethylacetate, preferably xylene. Suitable bases are for example sodium carbonate, sodium hydroxyde, triethylamine or pyridine, especially preferred bases are sodium hydroxyde and triethylamine.

The process according to the invention is especially suitable for the production of compounds of formula I, wherein at least one of $R_1$, $R_2$ and $R_3$ is different from hydrogen.

The process according to the invention is especially suitable for the preparation of compounds of formula I, wherein at least one of $R_1$, $R_2$ and $R_3$ is halogen.

Further compounds of formula I can be advantageously prepared, wherein $R_1$, $R_2$ and $R_3$ are halogen, especially $R_1$, $R_2$ and $R_3$ are chloro.

Compounds of formula V which can be advantageously prepared as intermediates for the process according to this invention are described in Table 1.

TABLE 1

Preferred compounds of formula V (V)

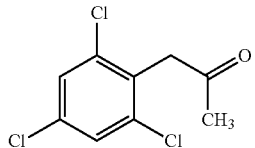

| No. | R₁ | R₂ | R₃ |
|---|---|---|---|
| 1.01 | Cl | Cl | Cl |
| 1.02 | Cl | H | Cl |
| 1.03 | Cl | Cl | H |
| 1.04 | Cl | Br | Cl |
| 1.05 | Br | Br | Br |
| 1.06 | H | Cl | H |
| 1.07 | H | Br | H |
| 1.08 | H | CF₃ | H |

PREPARATORY EXAMPLES

Example P1

Preparation of 1-(2,4,6-trichloro-phenyl)-propan-2-one (compound CAS1228284-86-3)

In a 1.5 l sulfonation flask equipped with mechanical stirring, cooling funnel, dropping funnel and thermometer under nitrogen at ambient temperature filled with acetone (240 ml), were added isopropenyl acetate (66 ml, 0.60 mol), tert-butyl nitrite (40 ml, 0.30 mol) and cupric sulfate pentahydrate (2.5 g, 0.001 mol). The resulting light green-blue suspension is stirred for 15 min at ambient temperature. A solution of 2,4,6-trichloroaniline (40 g, 0.20 mol), dissolved in acetone (320 ml) was added dropwise over a period of 2 hours. During the addition, bubbling observed, temperature rose to 30° C. and the mixture turned green. 1 Hour after the addition, an amber solution was obtained. The mixture was stirred for 6 hours. Completion of the reaction was confirmed by GC-MS. The crude mixture was concentrated under reduce pressure to remove most of the acetone and the residue was dissolved in ethyl acetate (300 ml) and wash with 1M hydrochloric acid (2×300 ml), water (2×300 ml) potassium carbonate solution (300 ml) followed by water (300 ml). Combined basic aqueous were re-extracted with of ethyl acetate (150 ml). Combined organics were dried over sodium sulfate, and the organics were concentrated under reduced pressure to give crude 1-(2,4,6-trichloro-phenyl)-propan-2-one (53 g) as a dark brown oil. The crude was dissolved again in ethyl acetate (200 ml) and washed with 1M sodium hydroxide (300 ml) 1M hydrochloric acid (100 ml) and water (200 ml). The organic layers were dried and evaporated to give crude 1-(2,4,6-trichloro-phenyl)-propan-2-one 49 g dark brown oil which crystallized.

¹H NMR (400 MHz, CDCl₃): δ2.26 (s, 3H, CH₃), 4.05 (s, 2H, CH₂), 7.34 (s, 2H, Ar—H)

Example P2

Preparation of 1-(4-bromo-2,6-dichloro-phenyl)-propan-2-one

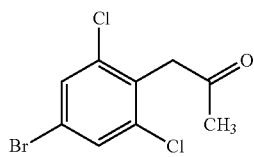

In a 50 ml three-neck flask equipped with mechanical stirring, cooling funnel, dropping funnel and thermometer under nitrogen at ambient temperature filled with acetonitrile (10 ml), were added cuprous oxide (1.5 g, 0.018 mol), isopropenyl acetate (13.6 ml, 0.125 mol) and tert-butyl nitrite (1.7 ml, 0.0125 mol). The resulting red suspension is stirred for 15 min at ambient temperature. A solution of 4-bromo-2,6-dichloroaniline (2.0 g, 0.0083 mol), dissolved in acetonitrile (15 ml) was added dropwise over a period of 20 minutes. During the addition, bubbling was observed. The mixture was stirred at 40° C. for 20 hours. The red crude mixture was passed through celite to remove solid particles and concentrated under reduce pressure to give a brown solid. The residue was dissolved in dichloromethane (120 ml) and washed with water (2×50 ml) and brine (40 ml). Organics were dried over sodium sulfate and concentrated under reduced pressure to give crude 1-(4-bromo-2,6-dichloro-phenyl)-propan-2-one (2.3 g) as a dark brown oil.

¹H NMR (400 MHz, CDCl₃): δ2.25 (s, 3H, CH₃), 4.06 (s, 2H, CH₂), 7.50 (s, 2H, Ar—H)

Example P3

Preparation of 1-(2,4,6-trichlorophenyl)-propan-2-one

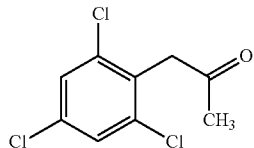

In a 50 ml three-neck flask equipped with stirring, cooling funnel, dropping funnel and thermometer under nitrogen at ambient temperature filled with acetonitrile (20 ml), isopropenyl acetate (31 g, 0.31 mol) and tert-amyl nitrite (3.6 g, 0.031 mol). The resulting suspension is stirred for 15 min at ambient temperature. A solution of 2,4,6-trichloroaniline (4.0 g, 0.020 mol), dissolved in acetonitrile (20 ml) was added dropwise over a period of 25 minutes. During the exothermic addition, bubbling was observed. The mixture was stirred at 40° C. for 1 hour. The volatiles were distilled off at 55° C. and 11 mbar. The residue was taken up with dichloromethane (50 ml) and washed with water (20 ml). The aqueous phase was extracted with an additional portion of dichloromethane (30 ml). The combined organic phases were then concentrated under reduced pressure to give a crude 1-(4-bromo-2,6-dichloro-phenyl)-propan-2-one (6.7 g, 34.8% GC; 48% yield) as a dark brown oil.

Example P4

Preparation of 1-(2,4,6-trichlorophenyl)-propan-2-one O-methyl-oxime (compound CAS 1228284-89-6)

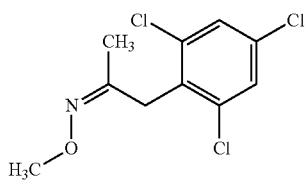

To a stirred solution of crude 1-(2,4,6-trichloro-phenyl)-propan-2-one prepared as described in example P1, (12 g, 0.050 mol) in methanol (100 ml) was added pyridine (6.8 ml, 0.084 mol), followed by O-methyl-hydroxylamine hydrochloride (6.70 g, 0.080 mol). The resulting mixture was stirred at ambient temperature for 18 hours. Methanol was removed under reduced pressure and the residue poured in 1N hydrochloric acid (300 ml) which was extracted with ethyl acetate (3×100 ml). Organics were combined, washed with brine, dried over sodium sulfate, filtered and evaporated under reduced pressure to give crude 1-(2,4,6-trichloro-phenyl)-propan-2-one O-methyl-oxime E/Z-mixture (12.3 g, 92%), which was taken up for the next reduction step.

Example P5

Preparation of 1-(2,4,6-trichlorophenyl)-propan-2-one O-methyl-oxime (compound CAS 1228284-89-6)

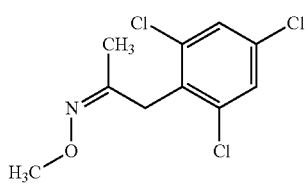

1-(2,4,6-trichloro-phenyl)-propan-2-one (273 g, 1.118 mol) was suspended in methanol (544 g) at ambient temperature. The resulting suspension was then heated under stirring to a temperature of 50° C. (most of the solid is dissolved). Then O-methyl-hydroxylamine hydrochloride as a 30% solution in water (358 g, 1.286 mol) was fed within 30-60 min. maintaining the temperature between 50-52° C. During the course of O-methyl-hydroxylamine hydrochloride addition the reaction mass turned into a two-phase system (liquid-liquid). At the end of O-methyl-hydroxylamine hydrochloride feed the pH was adjusted to 4-5 by slow addition of NaOH 30% (264 g 1.981 mol). The mixture was then stirred for 1-2 hours at 50-52° C. to allow the reaction to go to completion. Subsequently the pH was adjusted to 7-8 by adding NaOH 30% (8.5 g, 0.064 mol).

The product separated as a lower oily layer from the reaction mass in approx. 95% yield as a 2:1 mixture of E/Z-isomers.

Optionally the product can be extracted with a suitable solvent (e.g. hexane, methylcyclohexane, toluene). Depending on the quality requirements the resulting organic phase can be washed with water to remove residual sodium chloride.

$^1$H NMR (400 MHz, DMSO-d6): δ1.51 (s, 3H, minor-isomer), 1.82 (s, 3H, major-isomer), 3.62 (s, 3H, major-isomer), 3.74 (s, 2H, major-isomer), 3.80 (s, 3H, minor-isomer), 3.89 (s, 2H, minor-isomer), 7.64 (s, 2H, major-isomer), 7.70 (s, 2H, minor-isomer).

Example P6

Preparation of O-methyl-N-[1-methyl-2-(2,4,6-trichlorophenyl)-ethyl]-hydroxylamine (compound CAS 1228284-78-3)

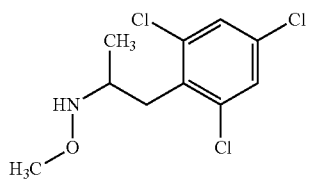

a) Sodium Cyanoborohydride:

To a stirred solution of crude 1-(2,4,6-trichloro-phenyl)-propan-2-one O-methyl-oxime prepared as described in example P4, (12.3 g, 0.046 mol) in acetic acid (120 ml), sodium cyanoborohydride (6.1 g, 0.097 mol) was added portionwise at 12 to 15° C. The reaction mass was stirred at ambient temperature for 18 hours. TLC confirmed the completion of reaction, then solvent was evaporated under reduced pressure (co-evaporation with toluene twice). The resulting residue was poured on to 1 N sodium hydroxide solution (150 ml) and extracted with dichloromethane (2×100 ml). The combined organic layer was washed with water (2×100 ml) followed by drying over anhydrous sodium sulfate before evaporating the solvent to afford crude O-Methyl-N-[1-methyl-2-(2,4,6-trichloro-phenyl)-ethyl]-hydroxylamine (12.3 g, 100%).

$^1$H NMR (400 MHz, CDCl$_3$): δ0.91-0.93 (d, 3H), 2.72-2.77 (dd, 1H), 2.98-3.03 (dd, 1H), 3.25-3.30 (m, 1H), 3.93 (s, 3H), 7.15 (s, 2H).

b) Triethylaminoborane.

To 1-(2,4,6-trichloro-phenyl)-propan-2-one O-methyl-oxime prepared as described in example P4 (53.9 g; assay 99%; 0.20 mol) in methanol (100 g) was added hydrogen chloride gas (22.0 g; 0.60 mol), whereas internal temperature in maintained at 20-30° C. by external cooling. A colourless suspension was obtained. The reaction mixture was cooled to 15° C. and triethylamino borane (borane triethylamine complex; 27.6 g; assay 96%; 0.23 mol) was dosed in during 60 min maintaining internal temperature at 15° C. The reaction mass was stirred for another 2 hours allowing the mixture to warm to ambient temperature. Thereafter almost no starting material can be detected by HPLC. The reaction mixture was then added to preheated (85° C.) water (126 g) during 30 min. A steady stream of gas was evolved; at the same time solvent was distilled. Heating was continued and the temperature maintained at 85-90° C. for another 1 hour. Finally gas was no longer produced. The resulting mixture was cooled to 20-25° C. Sodium hydroxide (30% aqueous solution; 56.5 g; 0.42 mol) was carefully added in order to bring pH to 7.2-7.7. The resulting mixture was extracted with tert-butyl methyl ether (125 ml). Phases were allowed to separate. The (lower) aqueous phase was split of. The (upper) organic phase was washed with water (2×100 g) and evaporated. Crude O-Methyl-N-[1-methyl-2-(2,4,6-trichloro-phenyl)-ethyl]-hydroxylamine (53.9 g; assay 97.8%; yield 98.0%) was obtained as clear oil.

c) Pt/H$_2$

To 1-(2,4,6-trichloro-phenyl)-propan-2-one O-methyl-oxime prepared as described in example P3 (54.2 g; assay 98.4%; 0.20 mol) in acetic acid (115 g; 1.92 mol) was added sulphuric acid (22.5 g; assay 96%; 0.22 mol) at such a rate that the mixture could be kept at 20-23° C. Platinum on charcoal (5.9 g; Evonik F101 N/W 5%, water wet; assay 2.32% Pt) was added. The resulting mixture was transferred to an autoclave, which then was sealed and pressurized with hydrogen (0.8 MPa). The agitator of the autoclave was started and hydrogen pressure is maintained at 0.8 MPa. When no more hydrogen is consumed (usually after 5 hours), hydrogenation was interrupted by stopping agitation. Pressure was released and the atmosphere in the autoclave changed to nitrogen. The hydrogenation mixture was filtered in order to remove the heterogenous catalyst. To the filtrate was added water (220 g) and a pH-probe was mounted. Aqueous sodium hydroxide (304 g; assay 30%; 2.28 mol) was fed until pH is above 9. The resulting mixture was extracted with tert-butyl methyl ether (300 ml). Phases were allowed to separate. The (lower) aqueous phase was separated and discarded. The organic phase was washed with water (2×250 g) and evaporated to dryness. Crude O-Methyl-N-[1-methyl-2-(2,4,6-trichloro-phenyl)-ethyl]-hydroxylamine (53.0 g; assay 93.7%; yield 92.4%) was obtained as clear oil.

Example P7

Preparation of 3-difluoromethyl-1-methyl-1H-pyrazole-4-carboxylic acid methoxy-[1-methyl-2-(2,4,6-trichlorophenyl)-ethyl]-amide (compound CAS1228284-64-7)

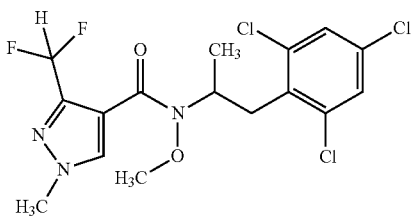 [SMILES: CON(C(=O)c1cn(C)nc1C(F)F)C(C)Cc1c(Cl)cc(Cl)cc1Cl]

Variant a):

To a solution of O-methyl-N-[1-methyl-2-(2,4,6-trichloro-phenyl)-ethyl]-hydroxylamine (12.3 g, 0.046 mol) prepared as described in example P5a, in dichloromethane (120 ml) was added triethylamine (7.7 ml, 0.055 mol) followed by dropwise addition of a solution of 3-difluoromethyl-1-methyl-1H-pyrazole-4-carbonyl chloride (9.1 g, 0.046 mol) in dichloromethane (10 ml) at 0° C. After complete addition of acid chloride the mixture was stirred 5 hours at ambient temperature. When the TLC confirmed completion of the reaction, the reaction mass was washed with 1N HCl (100 ml), followed by 1N NaOH (100 ml), then with water (2×100 ml) and finally with brine solution (50 ml) before drying over sodium sulfate and evaporation of the solvent. The resulting crude mass 20.5 g of a sticky dark brown oil was purified by column chromatography using 60-120µ mesh silica gel and product collected at 40% ethyl acetate in hexane as eluent to give 3-difluoromethyl-1-methyl-1H-pyrazole-4-carboxylic acid methoxy-[1-methyl-2-(2,4,6-trichloro-phenyl)-ethyl]-amide (7.9 g, 41%) as off white solid. m.p: 110-112° C. $^1$H NMR (400 MHz, CDCl$_3$): δ1.38-1.39 (d, 3H), 3.20-3.26 (dd, 1H), 3.32-3.37 (dd, 1H), 3.70 (s, 3H), 3.97 (s, 3H), 4.88-4.93 (m, 1H), 7.02-7.29 (t, 1H), 7.27 (s, 2H), 7.81 (s, 1H) MS [M+H]$^+$ 426/428/430

Variant b):

To a solution of O-methyl-N-[1-methyl-2-(2,4,6-trichloro-phenyl)-ethyl]-hydroxylamine (12.3 g, 0.046 mol) prepared as described in example P5a in Xylene (90 g) was added triethylamine (5.6 g, 0.055 mol) followed by addition of 3-difluoromethyl-1-methyl-1H-pyrazole-4-carbonyl chloride (40.1 g, 0.046 mol) at 70° C. during 2 hours. After complete addition of acid chloride the mixture was stirred 2 hours at 70° C. The solution was washed twice with water and the volatiles were removed from the organic layer under reduced pressure. The resulting crude mass 23.6 g (sticky dark brown oil) was purified by crystallization from a mixture of 16 g xylene and 36 g methylcyclohexene to give 3-difluoromethyl-1-methyl-1H-pyrazole-4-carboxylic acid methoxy-[1-methyl-2-(2,4,6-trichloro-phenyl)-ethyl]-amide (17.0 g, 91.5%) as off white solid. m.p: 115-116° C.

Variant c):

To a solution of O-methyl-N-[1-methyl-2-(2,4,6-trichloro-phenyl)-ethyl]-hydroxylamine (3.92 g, 0.014 mol) prepared as described in example P5a in xylene (30 g) was added an aqueous sodium hydroxide solution (30%, 2.3 g, 0.017 mol) in parallel to the addition of 3-difluoromethyl-1-methyl-1H-pyrazole-4-carbonyl chloride (3.2 g, 0.046 mol) dissolved in xylene (10 g) at 56° C. during 2 hours. After complete addition of acid chloride the mixture was stirred 2 hours at 56° C. The solution was washed twice with water (10 and 5 g) and the volatiles were removed from the organic layer under reduced pressure. The resulting crude mass 7.4 g (sticky dark brown oil) was purified by crystallization from a mixture of xylene (7 g) and methylcyclohexene (14 g) to give 3-difluoromethyl-1-methyl-1H-pyrazole-4-carboxylic acid methoxy-[1-methyl-2-(2,4,6-trichloro-phenyl)-ethyl]amide (5.3 g, 87.8%) as off white solid. m.p: 115-116° C.

What is claimed is:

1. A process for the preparation of the compound of formula I

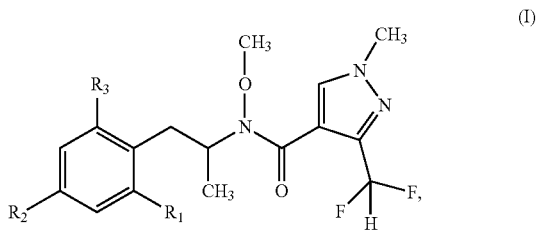

wherein $R_1$ is hydrogen, halogen or $C_1$-$C_6$alkyl;

$R_2$ is hydrogen, halogen, $C_1$-$C_6$alkyl, $C_2$-$C_6$alkenyl, $C_3$-$C_6$alkinyl, $C_3$-$C_6$cycloalkyl-$C_3$-$C_6$alkinyl, halophenoxy, halophenyl-$C_3$-$C_6$alkinyl, $C(C_1$-$C_4$alkyl)=NO—

$C_1$-$C_4$alkyl, $C_1$-$C_6$haloalkyl, $C_1$-$C_6$haloalkoxy, $C_2$-$C_6$haloalkenyl or $C_2$-$C_6$haloalkenyloxy; and $R_3$ is hydrogen, halogen or $C_1$-$C_6$alkyl;

which process comprises a) adding a compound of formula II

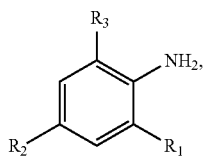
(II)

wherein $R_1$, $R_2$ and $R_3$ have the meanings as described under formula I, in the presence of an inert organic solvent to a mixture comprising an organic nitrite of formula III

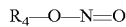
(III), wherein $R_4$ is $C_1$-$C_8$alkyl, a compound of formula IV

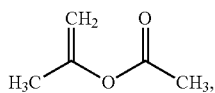
(IV)

and an inert organic solvent;

b) reacting the resulting compound of formula V

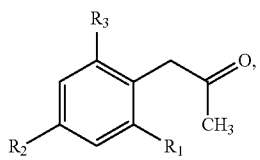
(V)

wherein $R_1$, $R_2$ and $R_3$ have the meanings as described under formula I with O-methyl-hydroxylamine of formula VI

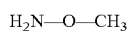
(VI), to the compound of formula VII

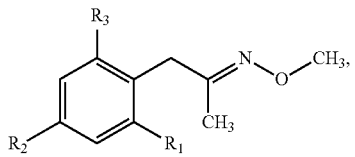
(VII)

wherein $R_1$, $R_2$ and $R_3$ have the meanings as described under formula I;

c) reducing the compound of formula VII to the compound of formula VIII

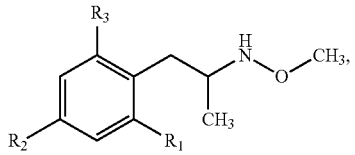
(VIII)

wherein $R_1$, $R_2$ and $R_3$ have the meanings as described under formula I d) and reacting the compound of formula VIII with a compound of formula IX

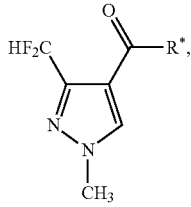
(IX)

in which R* is halogen, hydroxy or $C_{1-6}$ alkoxy to the compound of formula I.

2. A process according to claim 1 for the preparation of a compound of formula I, wherein at least one of $R_1$, $R_2$ and $R_3$ is different from hydrogen.

3. A process according to claim 1 for the preparation of a compound of formula I, wherein at least one of $R_1$, $R_2$ and $R_3$ is halogen.

4. A process according to claim 1 for the preparation of a compound of formula I, wherein $R_1$, $R_2$ and $R_3$ are chloro.

5. A process according to claim 1 for the preparation of a compound of formula I, wherein R is $C_4$-$C_7$alkyl.

* * * * *